(12) United States Patent
Eskilsson et al.

(10) Patent No.: US 11,138,429 B2
(45) Date of Patent: Oct. 5, 2021

(54) IRIS RECOGNITION USING EYE-TRACKING SYSTEM

(71) Applicant: Tobii AB, Danderyd (SE)

(72) Inventors: Henrik Eskilsson, Danderyd (SE); Mårten Skogö, Djursholm (SE)

(73) Assignee: Tobii AB, Danderyd (SE)

( * ) Notice: Subject to any disclaimer, the term of this patent is extended or adjusted under 35 U.S.C. 154(b) by 256 days.

(21) Appl. No.: 16/298,585

(22) Filed: Mar. 11, 2019

(65) Prior Publication Data

US 2019/0278987 A1    Sep. 12, 2019

Related U.S. Application Data

(60) Provisional application No. 62/641,765, filed on Mar. 12, 2018.

(51) Int. Cl.
| | |
|---|---|
| *G06K 9/00* | (2006.01) |
| *G06F 3/01* | (2006.01) |
| *G02B 27/01* | (2006.01) |
| *A61B 5/117* | (2016.01) |
| *G07C 9/37* | (2020.01) |

(52) U.S. Cl.
CPC ....... *G06K 9/00617* (2013.01); *G02B 27/017* (2013.01); *G06F 3/013* (2013.01); *G06K 9/00604* (2013.01); *A61B 5/117* (2013.01); *G02B 2027/014* (2013.01); *G02B 2027/0178* (2013.01); *G06K 9/0061* (2013.01); *G07C 9/37* (2020.01)

(58) Field of Classification Search
CPC .......... G06K 9/00617; G06K 9/00604; G06K 9/0061; G02B 27/017; G02B 2027/014; G02B 2027/0178; G06F 3/013; G07C 9/37; A61B 5/117
See application file for complete search history.

(56) References Cited

U.S. PATENT DOCUMENTS

| | | | |
|---|---|---|---|
| 8,824,779 B1* | 9/2014 | Smyth | G06T 7/593 |
| | | | 382/154 |
| 9,538,947 B2* | 1/2017 | Mori | A61B 5/16 |
| 9,607,138 B1* | 3/2017 | Baldwin | G06F 21/32 |
| 9,679,152 B1* | 6/2017 | Young | G06T 19/003 |
| 9,848,113 B2* | 12/2017 | Smits | G06K 9/228 |
| 10,013,055 B2* | 7/2018 | Perek | G06F 3/013 |
| 10,082,664 B2* | 9/2018 | Smits | G02B 27/644 |
| 10,241,545 B1* | 3/2019 | Richards | G06F 1/163 |
| 10,311,584 B1* | 6/2019 | Hall | G06T 7/251 |
| 10,334,240 B2* | 6/2019 | Zhao | H04N 13/246 |
| 10,650,609 B2* | 5/2020 | Kohlhoff | G06F 3/017 |
| 2015/0123991 A1* | 5/2015 | Yarosh | G02B 27/017 |
| | | | 345/629 |
| 2015/0124071 A1* | 5/2015 | DeLine | B60R 1/12 |
| | | | 348/78 |

(Continued)

*Primary Examiner* — Mia M Thomas
(74) *Attorney, Agent, or Firm* — Samuel I. Yamron (57) ABSTRACT

An eye-tracking system (e.g., a virtual reality or augmented realty headset) can be used for eye tracking and for iris recognition. Illuminators used to illuminate eyes of a user during eye tracking can be selectively powered on and off in connection with capturing image information in order to obtain image information that suitably depicts an iris region of an eye of the user. This image information can be used to recognize the iris region and by so doing authenticate and/or identify the user.

24 Claims, 6 Drawing Sheets

(56) References Cited

U.S. PATENT DOCUMENTS

| | | | | |
|---|---|---|---|---|
| 2015/0186711 A1* | 7/2015 | Baldwin | ............ | G06F 21/32 |
| | | | | 382/118 |
| 2016/0275483 A1* | 9/2016 | Zhou | ............ | G06Q 20/32 |
| 2017/0061210 A1* | 3/2017 | Ollila | ............ | H04N 1/00307 |
| 2017/0323167 A1* | 11/2017 | Mapen | ............ | G06T 7/90 |
| 2017/0340205 A1* | 11/2017 | Liu | ............ | A61B 3/113 |
| 2020/0143163 A1* | 5/2020 | Ackerman | ............ | G06K 9/00617 |

* cited by examiner

IRIS RECOGNITION USING EYE-TRACKING SYSTEM

CROSS-REFERENCE TO RELATED APPLICATIONS

This application claims the benefit of Provisional U.S. Patent Application No. 62/641,765 filed Mar. 12, 2018, the entire disclosure of which is hereby incorporated by reference, for all purposes, as if fully set forth herein.

BACKGROUND

A typical iris authentication system includes a camera that scans (e.g., takes one or more images) of an eye of a user (e.g., an iris region). Software then compares the images to an iris template to determine whether a match exists. For example, a mobile device such as a cell phone may have a dedicated iris authentication camera and/or may be configured to use a front-facing multipurpose camera.

DETAILED DESCRIPTION

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples described herein relate to systems, devices, and methods for performing iris authentication using a headset adapted for eye-tracking (e.g., eye-tracking system). For example, a virtual reality (VR) or augmented reality (AR) headset can include a camera (e.g., an infrared camera) positioned to capture images of at least one eye. Such a headset also includes a plurality of illuminators positioned to shine light on at least one eye of a user. For eye-tracking, the frequency at which the illuminators shine light on the eyes is coordinated with the frame rate of the camera capturing images of the eyes. The cornea of the eye reflects this light and creates corresponding reflective glints (e.g., reflections of fixed shape and size). These reflective glints are used to measure gaze (i.e., where the user is looking). The illuminators also light up the eye thereby increasing the amount of light present in the headset and improving the conditions for good quality images of the eye. The camera is used to capture images of the eye of the user including at least one reflective glint. Logic running on the headset is used to determine eye location based on positions of the at least one reflective glint with respect to portions of the eye.

Iris recognition approaches can be used to identify a user, authenticate the user, and perform actions with respect to the identity of the user. An example iris recognition approach is described herein. For example, the camera can capture images of the eye of the user, create a numerical representation, a template, of the iris and compare this to one or more stored templates to determine whether a match exists. In a VR headset, the illuminators are used to light up the eye of the user. This light may be helpful for obtaining quality image data of the eye for iris recognition. The reflective glints present in the eyes, however, may occlude portions of the iris resulting in unsatisfactory image data for iris identification. To address this, the techniques described herein dynamically and selectively illuminate the eye in a manner that produces satisfactory image data for iris identification.

The techniques described herein can include dynamically powering on and off certain illuminators while simultaneously capturing images of the eyes. For example, iris recognition may be performed using at least two images each being captured with at least partially different subsets of the illuminators lit. When the data from the images are combined they may capture the full iris in sufficient detail for recognition.

For instance, in a headset (either VR or AR) with 8 illuminators targeting at least one eye, a first image can be captured with illuminators 1, 3, 5, and 7 lit and a second image with illuminators 2, 4, 6, and 8 lit. Combining data from these images can ensure that all parts of the iris are "visible" to the iris recognition algorithm. If the headset also supports eye tracking, information about positions of each reflective glint, as well as identity of the illuminator causing this glint may be known. These positions can be used together with the image data to inform the iris identification algorithm what parts of each iris image to disregard (e.g., those that include reflective glints occluding the iris region of the eye).

The glint pattern (i.e., 2 or more glints) may also provide information about corneal curvature ensuring that an iris image (as opposed to an actual eye) could not be used to spoof the iris recognition algorithm (e.g., an authorized attempt to log into a device). For example, the glint pattern can be used to ascertain whether there is a curved cornea on top of the iris and any eye movement will move the glints differently than the iris (i.e., the glint will not remain at the same position on the iris when the eye moves (this is another way of doing anti-spoofing)).

In some examples, iris authentication may occur in a manner that is invisible to the user. For example, iris authentication may be performed as the user is playing a game or otherwise interacting with the headset. In some examples, at least some of the output from the camera used for eye tracking can also be used for iris authentication. In this manner, the two operations may be performed simultaneously. For example, eye-tracking may still be performed when selective subsets of the illuminators are being lit to capture images for iris authentication.

In some examples, the headset is configured to operate in an iris recognition mode and an eye-tracking mode. Predefined triggers may cause the headset to switch modes. Such triggers may include user inputs, computer application events, and other similar triggers. For example, logging into the headset device may be a trigger that causes iris authentication. Once authenticated, the headset may switch to the eye-tracking mode. In some examples, the eye-tracking mode is the default mode.

In some examples, especially in an VR headset, iris recognition can be improved by making the screen bright to make the pupil contract to facilitate iris recognition. In some examples, especially in an AR headset, similar pupil contraction can be stimulated through a see-through display or retinal projection (e.g., by creating a bright object or area in front of the user). These approaches may make the iris more visible but also show that the pupil is responsive and that the individual is alive. Thus, the techniques described herein can be used to determine whether a user is alive (e.g., to avoid spoofing).

In some examples, if the user is wearing regular glasses in a VR headset the techniques described herein may be able to cycle though illuminators to determine which illuminator that causes disturbing reflections in lenses of the glasses and thus exclude that/those illuminator/s from future exposures. In this case, the reflections in the lenses occur in addition to the reflective glints present in the eyes. The reflections in the lenses may cause difficulties during iris recognition (e.g., occlude portions of the iris) and during eye-tracking (e.g., occlude portions of the cornea).

The process of cycling through the illuminators, which may be used to improve iris recognition and eye-tracking, may begin by capturing image data depicting an eye and a lens of a pair of glasses with a first set of illuminators lit. The image data can be processed to identify reflections present in the lens and in the eye. This image data along with known positions of the illuminators of the first set can be used to identify associations between these illuminators and the reflections (e.g., which illuminators are causing which reflections). Once the associations have been identified, the approaches described herein can be used to selectively cycle through illuminators (e.g., power on/power off, adjust brightness, etc.), capturing different image data under the different conditions, and determine which illuminators to exclude from future exposures.

In some examples, individual eye characteristics of the user (personal eye parameters determined by calibration of the eye tracker) can be correlated with that of the individual identified through iris identification. For example, the foveal offset relative the optical axis can be seen if the user is looking at a fixation target. Other eye characteristics may be used for identification/authentication (e.g., the shape of the eye, visible veins, and other biometric measures).

Use of the system described herein improves the functioning of a computer by conserving processing resources. This may be achieved by performing iris identification using the same or similar data used for eye tracking. Because the computer is not required to change the exposure rates of cameras and illuminators, the process performs more efficiently than other conventional systems. In some examples, use of the system described herein may also provide for improved user experience as the user is unlikely to notice distinctions between when iris identification is being performed and eye tracking. Additionally, because of the quality of the image data that is being obtained, fewer processing resources are required to make determinations based on the data.

Figure 1:
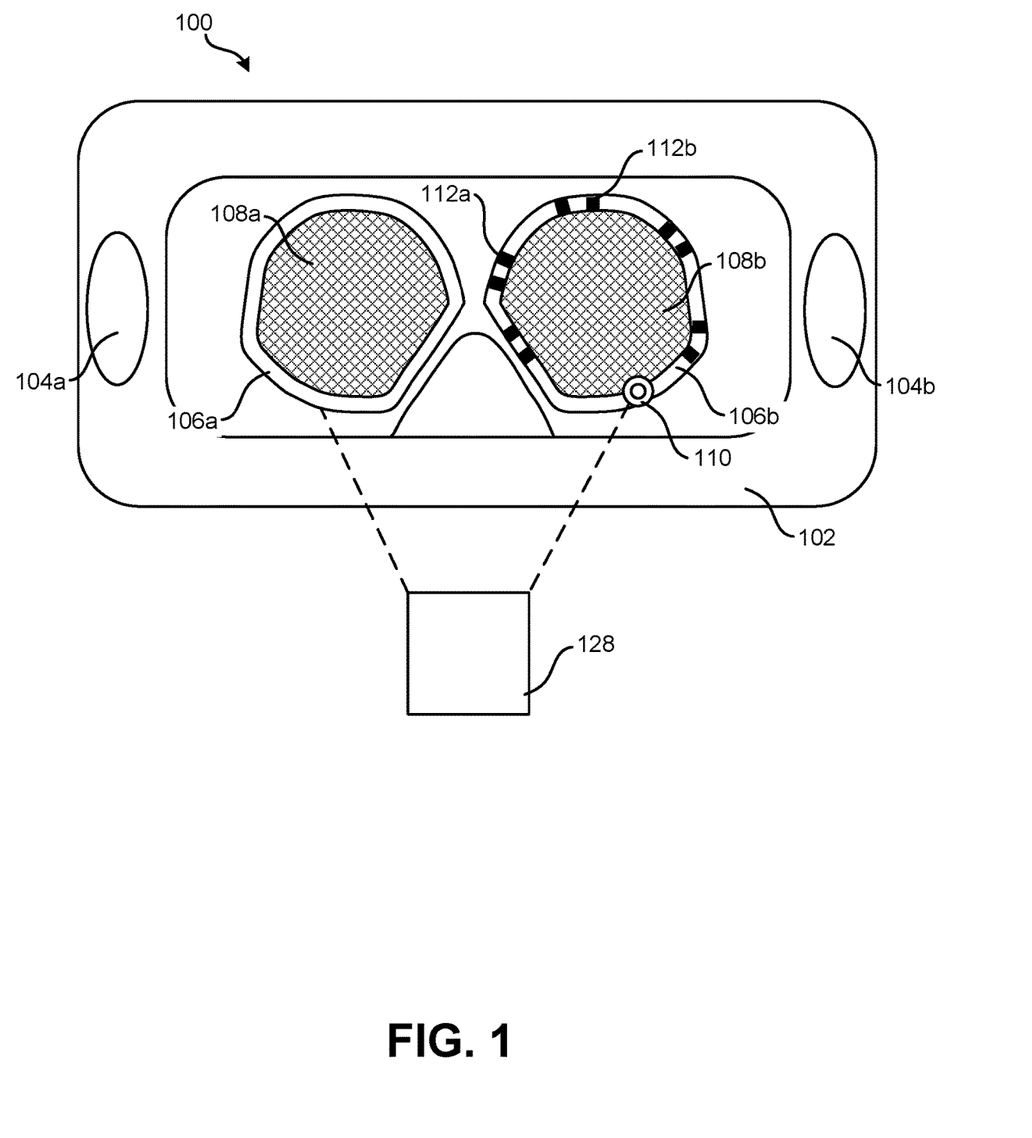
FIG. 1 illustrates an eye tacking system for implementing techniques for iris authentication, according to at least one example.

FIG. 1 illustrates an eye tacking system 100 (which may also be referred to as a gaze tracking system) for implementing the techniques described herein, according to an example. The system 100 may be implemented in a portable eye-tracking device such as a VR or AR headset. As such, the system 100 may include a frame 102 for supporting elements of the system. The frame 102 may also function to mount the system 100 to a head of the user. For example, the frame 102 may include mounting locations 104a, 104b for mounting a head strap to the frame 102. The head strap can include any suitable structure to mount the system 100 on the head of the user.

The system 100 also includes a pair of lens cups 106a, 106b each including a lens 108a, 108b. At least one of the lens cups 106 (e.g., the lens cup 106b) includes a camera module 110 and any suitable number of illuminators 112a-112N (e.g., 112a and 112b are labeled) surrounding the lens cup 106. In some examples, the lens cup 106a also includes an camera module and illuminators. The techniques described herein, however, may be implemented using image information of just one eye.

The illuminators 112 are configured to illuminate the eye of the user. The camera module 110 is configured to capture image data of the eye of the user. For example, the illuminators 112 may illuminate the eye of the user at least while the camera module 110 captures image data of the eye (e.g., for eye tracking and/or for iris recognition). The system 100 also includes displays disposed behind the lenses 108. In this manner, information may be presented on the displays in a manner that is viewable by the user through the lenses.

The illuminators 112 may be light emitting diodes or VCSELs emitting light in the near infrared frequency band. The camera module 110 may include for example a sensor, such as a complementary metal oxide semiconductor (CMOS) camera or a charged coupled device (CCD) camera.

Figure 2:
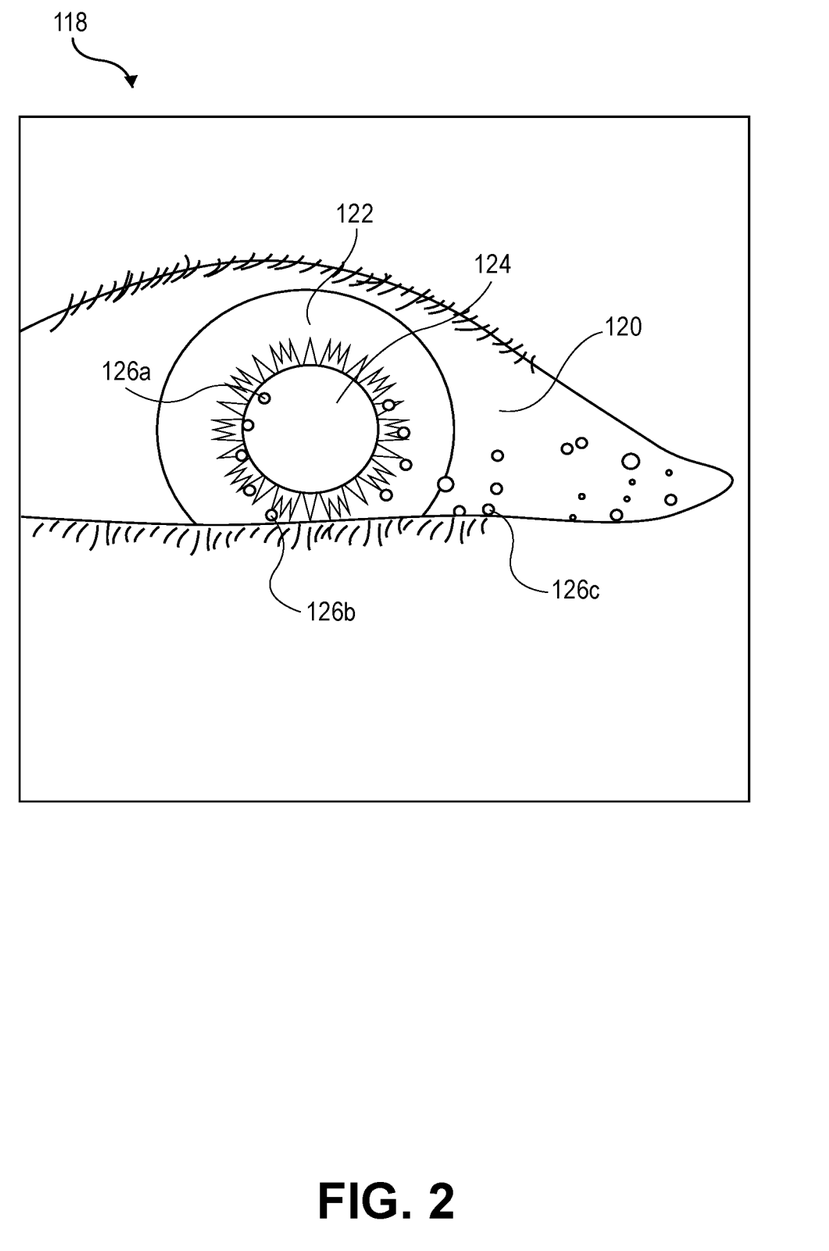
FIG. 2 illustrates an example eye, according to at least one example.

The illuminators 112 are arranged so as to provide illumination on different parts of the eye of the user. For example, FIG. 2 illustrates an example image of an eye 118 of a user. The eye 118 includes a sclera 120, an iris 122, and a pupil 124. The illuminators 112 may cause reflective glints 126a-126N (126a-126c are labeled) in the eye 118 of the user. For example, depending on the positioning of the illuminators 112 in the lens cup 106, characteristics of the eye 118 (e.g., eye shape and size, whether eyelid is open, closed, or partially open, etc.), and position of the parts of the eye 118 (e.g., where the eye is looking), the reflective glints 126 may be appear on the different parts of the eye 118. For example, the reflective glint 126a may appear on the pupil 124, the reflective glint 126b may appear on the iris 122, and the reflective glint 126c may appear in the sclera 120. As described herein, information about the positioning of the illuminators 112 and which reflective glint 126 is produced by which illuminator 112 may enable the system 100 to perform eye tracking techniques. In some examples, this same information may be used to determine to dynamically cycle through illuminators as part of a process for recognizing the iris 122.

Returning to the eye tracking system 100 in FIG. 1, the eye tracking system 100 may also include a management device 128 (circuitry including, for example, one or more processors) for processing the images captured by the camera module 110. The management device 128 may for example be connected to the camera module 110 and the illuminators 112 via a wired or a wireless connection. For example, the management device 128 may be mounted to the frame 102 or may be separate from the frame 102 (e.g., included in a separate device). In another example, the management device 128 in the form of one or more processors may be provided in one or more stacked layers below the light sensitive surface of the camera module 110. The management device 128 controls and/or otherwise manages aspects of the operation of the other electronic parts of the eye tracking system 100.

In the example described with reference to FIG. 1, the illuminators 112 are arranged in an eye tracking system 100 worn by a user. This arrangement serves only as an example. It will be appreciated that more or less any number of illuminators and camera modules may be employed for eye tracking, and that such illuminators and camera modules may be distributed in many different ways relative to displays watched by the user. It will be appreciated that the eye tracking scheme described in the present disclosure may for example be employed for remote eye tracking (for example in a personal computer, a smart phone, or integrated in a vehicle).

Figure 3:
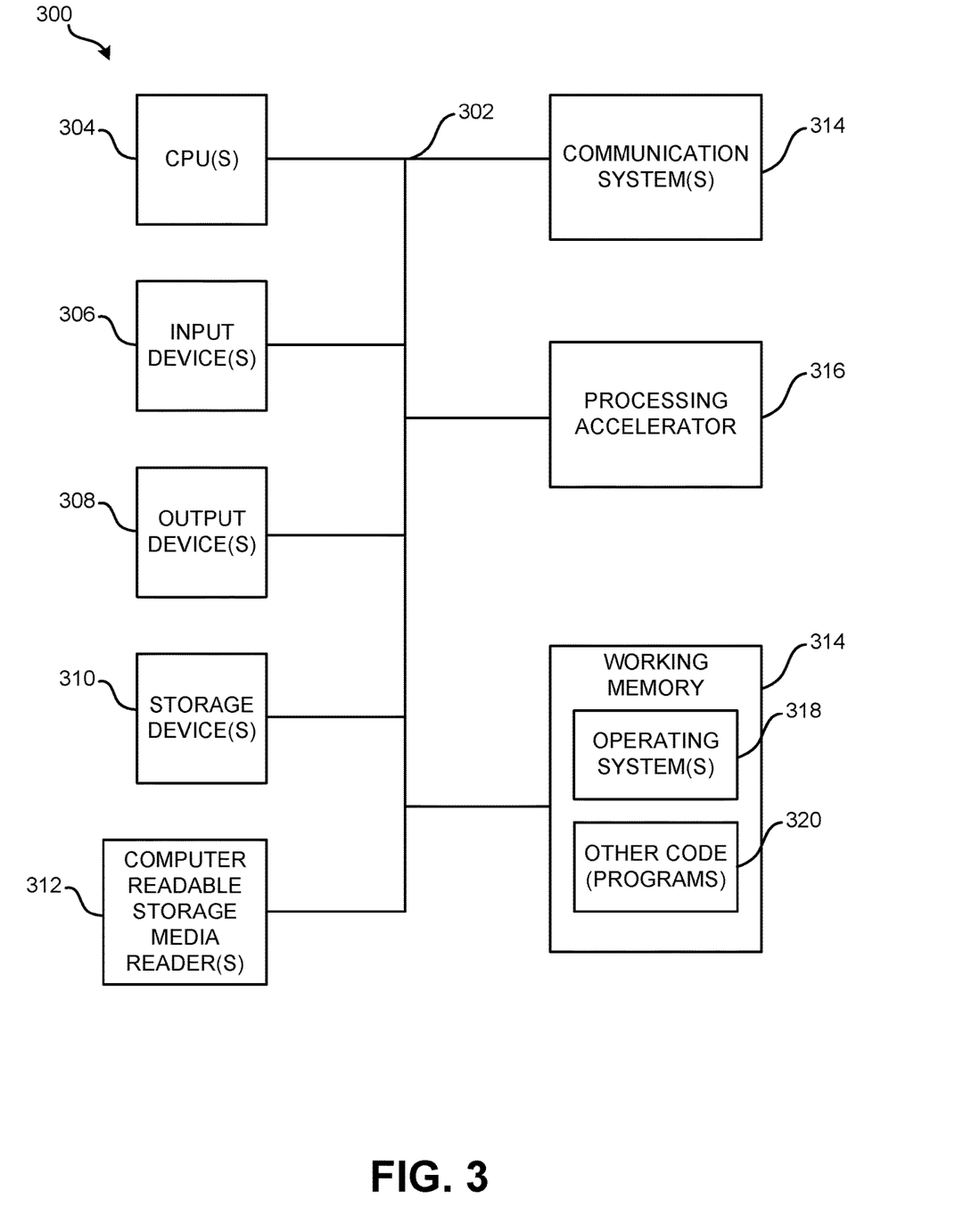
FIG. 3 illustrates a block diagram illustrating a specialized computer system for implementing techniques for iris authentication, according to at least one example.

FIG. 3 illustrates a block diagram illustrating a computer system 300 in which examples of the present disclosure may be implemented. This example illustrates computer system 300 such as may be used, in whole, in part, or with various modifications, to provide the functions of components described herein. For example, the illuminators 112, the management device 128, the display, and the camera module 110 may be implemented by the computer system 300. In some examples, the function of the management device 128 is distributed between one or more computer systems. For example, the illuminator 112, the display, the camera module 110, and a first set of functions of the management device 128 may be implemented as part of a head-mounted wearable device, and a second set of functions of the management device 128 may be implemented by a computer system that is in network communication with head-mounted wearable device.

The computer system 300 is shown including hardware elements that may be electrically coupled via a bus 302. In some examples, at least some of the hardware elements may be coupled together via a wireless or wired network connection (e.g., Bluetooth, WiFi, Zigbee, cellular, etc.) instead of the bus 302. For example, elements of the computer system 300 may be distributed between two or more devices (e.g., between a headset and a control computer). In some examples, at least some of the elements may be implemented using virtual computing resources.

The hardware elements may include one or more central processing units 304, one or more input devices 306 (e.g., a smartphone, a hand controller, an eye tracking device, etc.), and one or more output devices 308 (e.g., a display device, a printer, etc.). Specialized computer system 300 may also include one or more storage device(s) 310. By way of example, storage device(s) 310 may be disk drives, optical storage devices, solid-state storage device such as a random access memory ("RAM") and/or a read-only memory ("ROM"), which can be programmable, flash-updateable and/or the like.

Specialized computer system 300 may additionally include a computer-readable storage media reader 312, a communications system 314 (e.g., a modem, a network card (wireless or wired), an infra-red communication device, Bluetooth™ device, cellular communication device, etc.), and working memory 314, which may include RAM and ROM devices as described above. In some examples, specialized computer system 300 may also include a processing acceleration unit 316, which can include a digital signal processor, a general purpose graphical processing unit ("GPGPU"), a neural processing unit ("NPI"), a Convolutional Neural Network ("CNN") Processor, a special-purpose processor and/or the like.

Computer-readable storage media reader 312 can further be connected to a computer-readable storage medium, together (and, optionally, in combination with storage device(s) 310) comprehensively representing remote, local, fixed, and/or removable storage devices plus storage media for temporarily and/or more permanently containing computer-readable information. Communications system 314 may permit data to be exchanged with a network, system, computer and/or other component described above.

Specialized computer system 300 may also include software elements, shown as being currently located within a working memory 314, including an operating system 318 and/or other code 320. It should be appreciated that alternate examples of specialized computer system 300 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of specialized computer system 300 may include code 320 for implementing any or all of the function of the various elements of the architecture as described herein. For example, software, stored on and/or executed by a specialized computer system such as specialized computer system 300, can provide the functions of components of the disclosure such as those discussed above. Methods implementable by software on some of these components are discussed herein.

Figure 4:
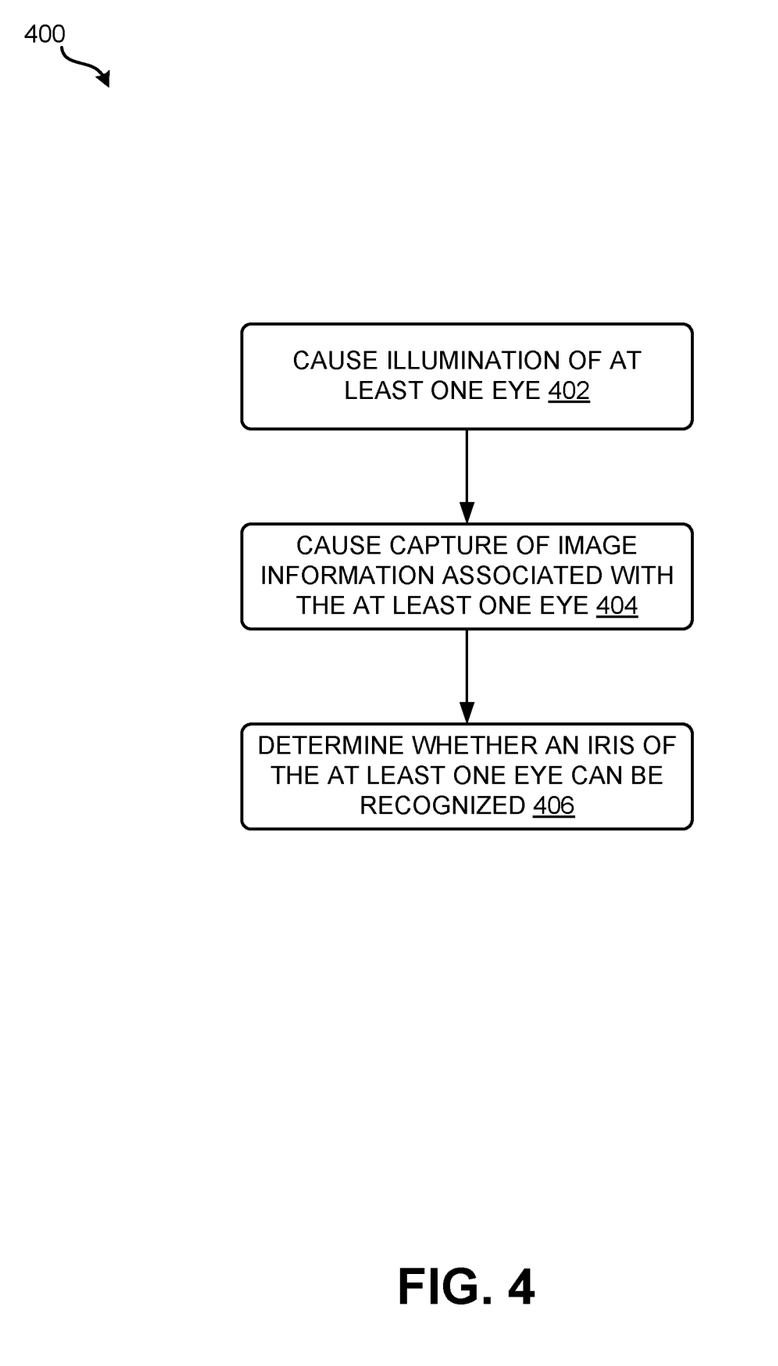
FIG. 4 illustrates an example flow diagram showing a process for iris authentication, according to at least one example.
Figure 5:
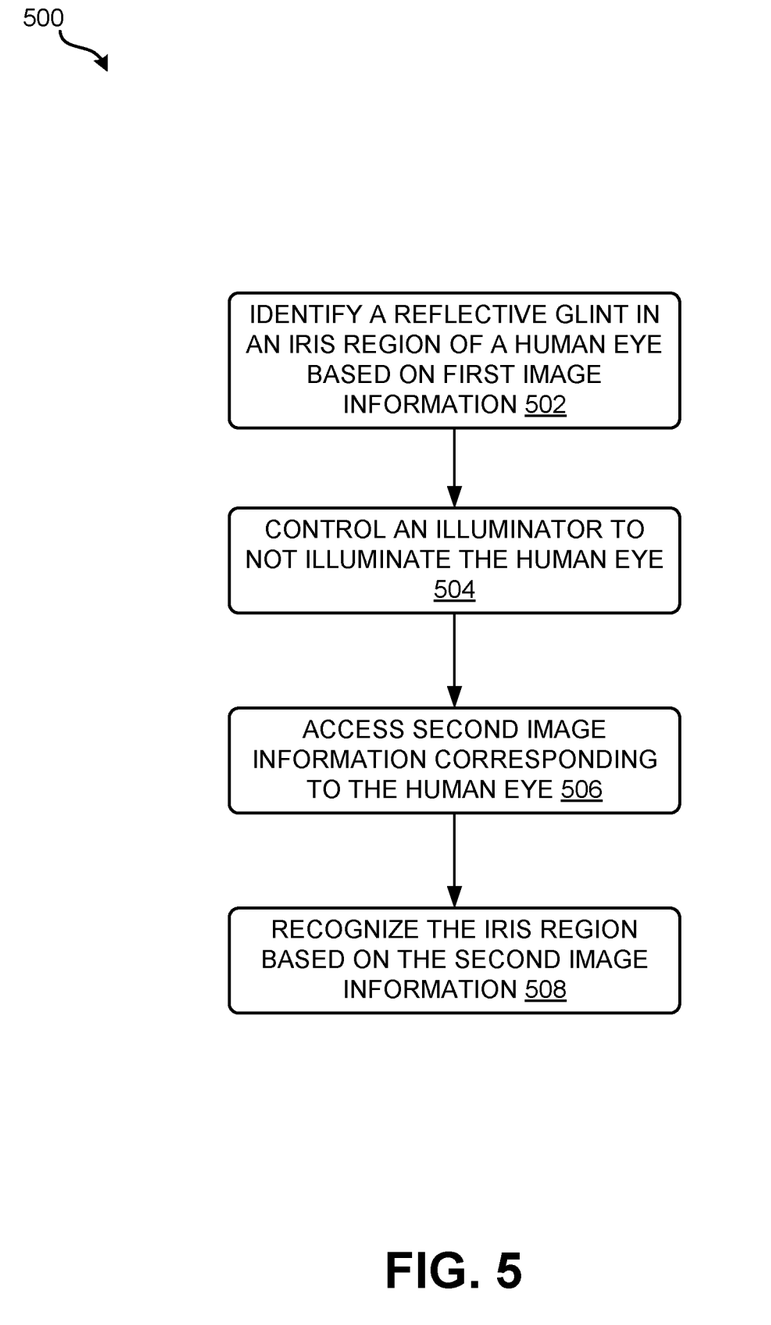
FIG. 5 illustrates an example flow diagram showing a process for iris authentication, according to at least one example.

FIGS. 3-5 illustrate example flow diagrams showing respective processes 300, 400, and 500 as described herein. The processes 300, 400, and 500 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

FIG. 4 illustrates a flow diagram depicting the process 400 for implementing techniques relating to iris authentication using a wearable device including an camera module and one or more illuminators (e.g., the system 100), according to at least one example. The wearable device may include, for example, a head-mounted wearable device, a wrist-worn wearable device, glasses, and other devices that can be mounted adjacent to and/or worn by a person. The management device 128 performs the process 400 of FIG. 4.

The process 400 begins at 402 by causing illumination of at least one eye. In some examples, this may be performed by the management device 128 instructing a set of illuminators of a plurality of illuminators that is connected to a wearable device and configured to illuminate the at least one eye. The plurality of illuminators may be positioned on the wearable device to project light onto the at least one eye of the user.

In some examples, causing the illumination of the at least one eye includes selecting the set of illuminators based at least in part on the management device operating in a recognition mode. In this example, the management device may further be configured to operate in an eye tracking mode for tracking movement of the at least one eye.

In some examples, causing the illumination of the at least one eye may further include selecting a percentage of the illuminators to light up the at least one eye (e.g., <90% of the total number of illuminators directed at the at least one eye, <80%, <70%, <60%, <50%, <40% or <30% of the total number of illuminators directed at the at least one eye are lit) In some examples, causing the illumination of the at least one eye may further include selecting a specific percentage corresponding to total light output for each illuminator and/or for a set of illuminators (e.g., <90%, <80%, <70%, <60%, <50%, etc.).

In some examples, the set of illuminators is predefined for recognizing the iris. For example, it may be determined at an earlier time which of the plurality of illuminators is best suited for iris recognition. These illuminators may constitute the set of illuminators used at 402.

At 404, the process 400 may include causing capture of image information associated with the at least one eye during the illumination of the at least one eye. In some examples, this may be performed by the management device instructing a camera of the wearable device to capture the image information. The camera may be connected to the wearable device and configured to capture images of the at least one eye of the user.

At 406, the process 400 may include determining whether an iris of the at least one eye can be recognized. In some examples, this may be performed by the management device based at least in part on the image information. This may include determining whether reflective glints created by the illuminators occlude essential parts of the iris. If so, the process 400 may include causing a subset of the illuminators to power off, causing the camera to capture additional image information, and determining again whether the iris can be recognized.

In some examples, the process 400 may further include recognizing the iris based at least in part on the image information. This may include recognizing the iris as one belonging to the user associated with the wearable device. Once suitable image information has been obtained using the techniques described herein, any suitable iris recognition approach may be performed. For example, this may include comparing the image information with stored image information to identify a match between the iris represented in the image information with an iris represented in the stored image information. Alternatively, or preferably an iris template extracted from the iris image is compared with a stored iris template.

In some examples, the process 400 may further include causing, by a different set of illuminators of the plurality of illuminators, a different illumination of the at least one eye. In this example, the process 400 may further include causing, by the camera, capture of different image information associated with the at least one eye during the different illumination of the at least one eye. In this example, recognizing the iris of the at least one eye may further be based at least in part on the different image information. In some examples, causing the different illumination and capture of the different image information is performed when the iris cannot be authenticated based at least in part on the image information.

In some examples, the wearable device further includes a display connected to the frame, or a retinal projection system making the user perceive a virtual display. In this example, the process 400 may further include causing, by the display, presentation of a target on the display. In this example, the process 400 may further include capturing, by the camera, different image information associated with the at least one eye while the target is being presented on the display, and determining eye characteristic information based on the different image information. In this example, recognition of the iris of the at least one eye may be based at least in part on the image information. In this example, the process 400 may further include identifying an identity of the user based at least in part on authenticating the iris of the at least one eye. In this example, the process 400 may further include determining that the eye characteristic information is associated with the individual whose iris has been recognized. The eye characteristic information may include at least one of: a foveal offset relative to an optical axis of the at least one eye, a shape of the at least one eye, a surface area of the at least one eye, or visible veins in the at least one eye. This additional biometric data can be used as anti-spoofing to ensure that no unauthorized person is trying to access the system with for instance an image of an authorized iris or contact lenses with the image of an authorized iris printed on it.

FIG. 5 illustrates a flow diagram depicting the process 500 for implementing techniques relating to iris recognition using a wearable device including a camera module and one or more illuminators (e.g., the system 100), according to at least one example. The management device 128 may perform the process 500 of FIG. 5.

The process 500 begins at 502 by identifying a reflective glint disposed within an iris region of a human eye based at least in part on first image information. This may be performed by the management device. The first image information may correspond to the human eye and may be collected by a camera module of a wearable device.

At 504, the process 500 may include controlling an illuminator of the wearable device to not illuminate the human eye. This may be performed by the management device 128. This may be based at least in part on determining that the reflective glint identified at 502 was caused by the illuminator. Block 504 may be performed in response to a failed iris recognition attempt based on the first image information. This attempt may have failed because the reflective glint occluded a portion of the iris region needed for iris recognition.

At 506, the process 500 may include accessing second image information corresponding to the human eye. This may be performed by the management device. The second image information may exclude the reflective glint and may have been obtained at least while the illuminator was not illuminating the human eye. In some examples, the first image information and the second image information is accessed from a camera module of the wearable device.

At 508, the process 500 may include recognizing the iris region based at least in part on the second image information. This may be performed by the management device.

In some examples, the illuminator is one of a plurality of illuminators configured to illuminate the human eye so as to create a plurality of reflective glints within the human eye. In this example, controlling the illuminator to not illuminate the human eye is based at least in part on determining that the reflective glint associated with the illuminator occludes at least a portion of the iris region.

In some examples, the reflective glint is a first reflective glint. In this example, the second image information includes a second reflective glint. In some examples, the second reflective glint is present in the first image information.

In some examples, the process 500 may further include causing a display of the wearable device to display an image. In this example, capturing the second image information is performed at least while the display is displaying the image. In some examples, capturing the second image information is performed after the display is no longer displaying the image. This may cause a pupil to contract revealing a larger portion of the iris region. In some examples, the process 500 may further include determining that a human user is alive based at least in part on causing the pupil region of the human eye to contract.

Figure 6:
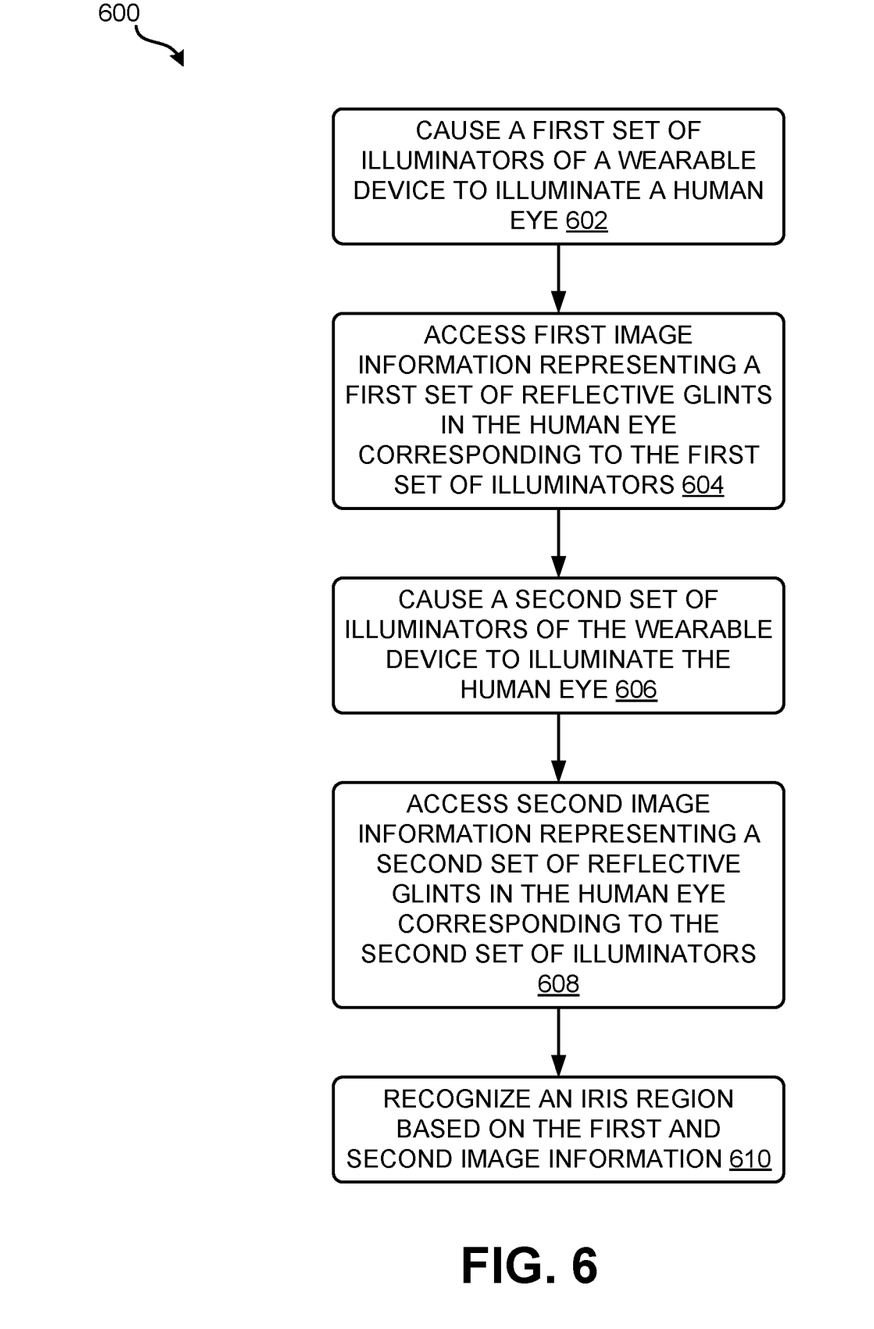
FIG. 6 illustrates an example flow diagram showing a process for iris authentication, according to at least one example.

FIG. 6 illustrates a flow diagram depicting the process 600 for implementing techniques relating to iris recognition using a wearable device including a camera module and one or more illuminators (e.g., the system 100), according to at least one example. The management device 128 may perform the process 600 of FIG. 6.

The process 600 begins at 602 by causing a first set of illuminators of a wearable device to illuminate a human eye. This may be performed by the management device. The human eye may include an iris region.

At 604, the process 600 may include accessing first image information including representation of a first set of reflective glints in the human eye corresponding to the first set of illuminators. This may be performed by the management device.

At 606, the process 600 may include causing a second set of illuminators of the wearable device to illuminate the human eye. This may be performed by the management device.

At 608, the process 600 may include accessing second image information including representation of a second set of reflective glints in the human eye corresponding to the second set of illuminators. This may be performed by the management device.

At 610, the process 600 may include recognizing the iris region based at least in part on the first image information and the second image information. This may be performed by the management device. In some examples, recognizing the iris region based at least in part on the first image information and the second image information includes identifying first positions of the first set of reflective glints in the human eye based at least in part on the first image information, excluding a first portion of the first image information to define information associated with a first remaining portion of the human eye based on the first positions, identifying second positions of the second set of reflective glints in the human eye based at least in part on the second image information, excluding a second portion of the second image information to define information associated with a second remaining portion of the human eye based on the second positions, and using the information associated with the first and second remaining portions of the human eye to recognize the iris region.

In some examples, recognizing the iris region may include creating an iris template based on the first image information and the second image information and comparing the image template with at least one stored iris template to determine whether a stored iris template matches the iris template.

In some examples, the first set of illuminators is distinct from the second set of illuminators. For example, the first set of illuminators can be a non-overlapping set as compared to the second set of illuminators.

In some examples, the process 600 further includes determining radial curvature information for the cornea based at least in part on two or more reflective glints from at least one of the first set of reflective glints or the second set of reflective glints. In this example, recognizing the iris region is further based at least in part on the radial curvature information of the cornea. This additional information can be used to authenticate and/or identify the person to whom the cornea belongs.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

What is claimed is:
1. A system comprising:
  a camera configured to capture images of at least one eye of a user;

a plurality of illuminators configured to project light toward the at least one eye of the user; and a management device in communication with the camera and the plurality of illuminators, the management device configured to:
- cause, by a set of illuminators of the plurality of illuminators, illumination of the at least one eye, wherein the set of illuminators comprises a specific percentage of the plurality of illuminators;
- cause, by the camera, capture of image information associated with the at least one eye during the illumination of the at least one eye; and
- determine whether an iris of the at least one eye can be recognized based at least in part on the image information.

2. The system of claim 1, wherein the management device is distributed between two or more electronic devices.

3. The system of claim 1, wherein causing the illumination of the at least one eye comprises selecting the set of illuminators based at least in part on the management device operating in a recognition mode.

4. The system of claim 1, wherein the management device is further configured to:
- receive other image information from the camera prior to causing illumination of the at least one eye; and
- determine the set of illuminators based at least in part on the other image information.

5. The system of claim 1, wherein the management device is further configured to authenticate an identity of a human based at least in part on recognizing the iris.

6. The system of claim 1, wherein:
the management device is further configured to:
- cause, by a different set of illuminators of the plurality of illuminators, a different illumination of the at least one eye;
- cause, by the camera, capture of different image information associated with the at least one eye during the different illumination of the at least one eye; and
- authenticate the iris of the at least one eye is based at least in part on the different image information.

7. The system of claim 6, wherein causing the different illumination and capture of the different image information is performed when the iris cannot be recognized based at least in part on the image information.

8. The system of claim 1, wherein:
the system further comprises a display; and
the management device is further configured to:
- cause, by the display, presentation of a target on the display;
- capture, by the camera, different image information associated with the at least one eye while the target is being presented on the display; and
- determine eye characteristic information based at least in part on the different image information.

9. The system of claim 8, wherein the management device is further configured to:
- identify an identity of a user based at least in part on recognizing the iris; and
- authenticate the identity of the user based at least in part on the eye characteristic information.

10. The system of claim 8, wherein the eye characteristic information comprises at least one of:
- a foveal offset relative to an optical axis of the at least one eye; or
- a curvature of a cornea of the at least one eye;
- a position of the cornea with respect to the iris of the at least one eye; or
- visible veins in the at least one eye.

11. The system of claim 1, wherein:
the system further comprises a display; and
the management device is further configured to present an image on the display that causes a pupil region of the at least one eye to contract.

12. The system of claim 11, wherein the management device is further configured to determine that the user is alive based at least in part on causing the pupil region of the at least one eye to contract.

13. A computer-implemented method, comprising:
- identifying a reflective glint disposed within an iris region of a human eye based at least in part on first image information corresponding to the human eye;
- controlling an illuminator to not illuminate the human eye based at least in part on (i) determining that the illuminator caused the reflective glint and (ii) determining that the reflective glint associated with the illuminator occludes at least a portion of the iris region, wherein the illuminator is one of a plurality of illuminators configured to illuminate the human eye so as to create a plurality of reflective glints within the human eye;
- accessing second image information corresponding to the human eye, the second image information excluding the reflective glint and being obtained at least while the illuminator was not illuminating the human eye; and
- recognizing the iris region based at least in part on the second image information.

14. The computer-implemented method of claim 13, wherein the reflective glint is a first reflective glint; and
wherein the second image information includes a second reflective glint.

15. The computer-implemented method of claim 13, further comprising:
- causing a display to display an image; and
- capturing the second image information at least while the display is displaying the image.

16. The computer-implemented method of claim 15, wherein displaying the image causes a pupil region of the human eye to contract.

17. The computer-implemented method of claim 16, further comprising determining that a human user is alive based at least in part on causing the pupil region of the human eye to contract.

18. A computer-implemented method, comprising:
- causing a first set of illuminators of a wearable device to illuminate a human eye comprising an iris region;
- accessing first image information including representation of a first set of reflective glints in the human eye corresponding to the first set of illuminators;
- causing a second set of illuminators of the wearable device to illuminate the human eye;
- accessing second image information including representation of a second set of reflective glints in the human eye corresponding to the second set of illuminators; and
- recognizing the iris region based at least in part on the first image information and the second image information.

19. The computer-implemented method of claim 18, wherein recognizing the iris region comprises:
- combining the first image information and the second image information to create combined image information; and
- recognizing the iris region based at least in part on the combined image information.

20. The computer-implemented method of claim 18, wherein the first set of illuminators is distinct from the second set of illuminators.

21. The computer-implemented method of claim 18, wherein recognizing the iris region based at least in part on the first image information and the second image information comprises:
    identifying first positions of the first set of reflective glints in the human eye based at least in part on the first image information;
    excluding a first portion of the first image information to define information associated with a first remaining portion of the human eye based on the first positions;
    identifying second positions of the second set of reflective glints in the human eye based at least in part on the second image information;
    excluding a second portion of the second image information to define information associated with a second remaining portion of the human eye based on the second positions; and
    using the information associated with the first and second remaining portions of the human eye to recognize the iris region.

22. The computer-implemented method of claim 18, further comprising determining radial curvature information based at least in part on two or more reflective glints from at least one of the first set of reflective glints or the second set of reflective glints.

23. The computer-implemented method of claim 22, wherein recognizing the iris region is further based at least in part on the radial curvature information.

24. The computer-implemented method of claim 18, wherein recognizing the iris region further comprises:
    creating a first iris template based at least in part on the first image information and the second image information, the first iris template comprising a first digital representation of the iris region;
    comparing the first iris template with at least one stored iris template to determine whether a stored iris template matches the first iris template; and
    recognizing the iris region when a match is identified based at least in part on comparing the first iris template with the stored iris template.

* * * * *